(12) United States Patent
Peppas et al.

(10) Patent No.: US 10,265,405 B2
(45) Date of Patent: Apr. 23, 2019

(54) POLYMERS FOR DELIVERY OF FACTOR VIII AND/OR FACTOR IX

(71) Applicant: Board of Regents, The University of Texas System, Austin, TX (US)

(72) Inventors: Nicholas A. Peppas, Austin, TX (US); Sarena D. Horava, Austin, TX (US)

(73) Assignee: BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 14/944,173

(22) Filed: Nov. 17, 2015

(65) Prior Publication Data

US 2016/0136291 A1 May 19, 2016

Related U.S. Application Data

(60) Provisional application No. 62/081,460, filed on Nov. 18, 2014.

(51) Int. Cl.
*A61K 47/48* (2006.01)
*A61K 9/00* (2006.01)
*A61K 38/48* (2006.01)
*A61K 47/60* (2017.01)
*A61K 47/58* (2017.01)
*A61K 47/69* (2017.01)

(52) U.S. Cl.
CPC ...... *A61K 47/48176* (2013.01); *A61K 9/0053* (2013.01); *A61K 38/4846* (2013.01); *A61K 47/58* (2017.08); *A61K 47/60* (2017.08); *A61K 47/6903* (2017.08); *C12Y 304/21022* (2013.01)

(58) Field of Classification Search
CPC ......... A61K 47/48176; A61K 38/4846; A61K 47/48215; A61K 9/0053
See application file for complete search history.

(56) References Cited

U.S. PATENT DOCUMENTS

2011/0227990 A1* 9/2011 Kuwabara ............ C08F 265/04
347/20

FOREIGN PATENT DOCUMENTS

| WO | WO 98/43615 | 10/1998 |
| WO | WO 2007/149406 | 12/2007 |
| WO | WO 2008/055254 | 5/2008 |

OTHER PUBLICATIONS

Kim et al., "Poly(ethylene glycol)-containing hydrogels for oral Protein Delivery Applications", Biomedical Microdevices, 5:4, 333-341, 2003.*
Foss et al., "Development of acrylic-based copolymer for oral insulin delivery", European Journal of Pharmaceutics and Biopharmaceutics 57 (2004), 163-169.*
(Continued)

*Primary Examiner* — Jianfeng Song
(74) *Attorney, Agent, or Firm* — Parker Highlander PLLC

(57) ABSTRACT

In some aspects, a composition comprising a pH-sensitive crosslinked copolymer of methacrylic acid and poly(ethylene glycol) monomethyl ether methacrylate and a therapeutic protein is provided. In some embodiments, the therapeutic protein is a high molecular weight protein such as factor VIII or factor IX. In some embodiments, the composition is orally administered to a patient to treat a disease or disorder such as, e.g., hemophilia.

22 Claims, 9 Drawing Sheets

(56) References Cited

OTHER PUBLICATIONS

Chang et al., "Sustained Release of Transgenic Human Factor IX: Preparation, Characterization, and in Vivo Efficacy", Molecular Pharmaceutics, 2011, 8, 1767-1774.*
Philips et al., "In vitro Evaluation of Carbohydrate Decorated-Hydrogels for oral Protein Delivery", Transactions of the Annual Meeting of the Society for Biomaterials (2010), 32 (Annual Meeting of the Society for Biomaterials: Giving Life to a World of Materials, 2010, vol. 1), 98. (Year: 2010).*
Trujillo-Lemon et al., "pH-Responsive Hydrogel with controlled Swelling and Degradation Rate", NSTI-Nanotech 2005, www.nsti.org , ISBN 0-9767985-0-6, vol. 1, 148-151. (Year: 2005).*
Carr and Peppas, "Assessment of poly(methacrylic acid-co-N-vinyl pyrrolidone) as a carrier for the oral delivery of therapeutic proteins using Caco-2 and HT29-MTX cell lines", *J Biomed. Mater. Res.* 92A, 504-512, 2010.
Carr et al., "Complexation Hydrogels for the Oral Delivery of Growth Hormone and Salmon Calcitonin", *Ind. Eng. Chem. Res.* 49, 11991-11995, 2010.
Dimitrov, "Therapeutic Proteins", *Methods Mol. Biol.* 899: 1-26, 2012.
Dobić et al., "Synthesis and characterization of poly(2-hydroxyethyl methactylate/itaconic acid/poly(ithylene glycol) dimethacrylate) hydrogels", *Chemical Engineering Journal* 179: 372-380, 2012.
Dressman and Kramer, "Pharmaceutical Dissolution Testing", Taylor & Francis, Boca Raton, FL, 2005.
Foss and Peppas, "Investigation of the cytotoxicity and insulin transport of acrylic-based copolymer protein delivery systems in contact with caco-2 cultures", *Eur. J. Pharm. Biopharm.* 57, 447-455, 2004.
Gupta et al., "Oral delivery of therapeutic proteins and peptides: a review on recent developments", *Drug Deliv.* 20, 237-246, 2013.
Kamei et al., "Complexation hydrogels for intestinal delivery of interferon β and calcitonin", *J. Control. Release* 134, 98-102, 2009.
Kavimandan et al., "Novel delivery system based on complexation hydrogels as delivery vehicles for insulin-transferrin conjugates", *Biomater.* 27, 3846-3854, 2006.
Leader et al., "Protein therapeutics: a summary and pharmacological classification", *Nat. Rev.* 7, 21-39, 2008.
Lowman et al., "Oral Delivery of Insulin Using pH-Responsive Complexation Gels", *J. Pharm. Sci.* 88, 933-937, 1999.
Morishita and Peppas, "Is the oral route possible for peptide and protein drug delivery?", *Drug Discov. Today* 11, 905-910, 2006.
Mullard, A., 2013. 2012 FDA drug approvals. *Nat. Rev. Drug Discov.* 12, 87-90.
Peppas et al., "Hydrogels in pharmaceutical formulations", *European Journal of Pharmaceutics and Biopharmaceutics* 50: 27-46, 2000.
Peyrot et al., "Correlates of insulin injection omission", *Diabetes Care* 33, 240-245, 2010.
Renukuntla et al., "Approaches for enhancing oral bioavailability of peptides and proteins", *Int. J. Pharm.* 447, 75-93, 2013.
Salama et al., "Tight junction modulation and its relationship to drug delivery", *Adv. Drug Deliv. Rev.* 58, 15-28, 2006.
Wood et al., "Lectin functionalized complexation hydrogels for oral protein delivery", *Journal of Controlled Release*, 116(2): e66-e68, 2006.
Wood et al., "The effect of complexation hydrogels on insulin transport in intestinal epithelial cell models", *Acta Biomaterialia*, 6: 48-56, 2010.
Wood et al., "Wheat germ agglutinin functionalized complexation hydrogels for oral insulin delivery", *Biomacromolecules*, 9:1293-1298, 2008.

\* cited by examiner

POLYMERS FOR DELIVERY OF FACTOR VIII AND/OR FACTOR IX

This application claims the benefit of U.S. Provisional Patent Application No. 62/081,460, filed Nov. 18, 2014, the entirety of which is incorporated herein by reference.

This invention was made with government support under Grant no. R01 EB000246 awarded by the National Institutes of Health and Grant No. DGE1110007 awarded by the National Science Foundation. The government has certain rights in the invention.

BACKGROUND OF THE INVENTION

1. Field of the Invention

The present invention relates generally to the field of pharmaceutics, polymer chemistry, and medicine. More particularly, it concerns pH-sensitive hydrogels that may be used to deliver large molecular weight therapeutic proteins to a subject.

2. Description of Related Art

Protein therapy can offer a number of advantages in disease treatment that cannot be matched by traditional therapy with small molecule drugs. The complexity of macromolecules can afford protein therapeutics high specificity to their target that can prevent widespread systemic side effects, yielding well-tolerated, highly active, and effective treatment options for a variety of diseases (Leader et al., 2008). Because of these benefits, protein-based drugs have remained one of the most common classes of newly FDA-approved drugs in recent years, accounting for 23% of new drugs in 2012 (Milliard, 2013) and 20% of new drugs in 2011 (U.S. Food and Drug Administration, 2012). Since recombinant insulin was first approved in 1982, the field has expanded to over 150 different FDA-approved protein therapeutics that accounted for $108 billion in sales in 2010 (Dimitrov, 2012).

Unfortunately, therapeutic proteins are primarily administered via injection only. Because protein therapeutics most frequently require repeated administrations, the cumulative frustration with a painful and inconvenient administration method often causes patients to intentionally skip injections, leading to less effective treatment (Peyrot et al., 2010). Oral delivery is a more desirable route of administration due to its ease, familiarity, and avoidance of chronic irritation (as experienced with injection or intranasal delivery methods). Additionally, oral delivery often offers lower cost, as orally-delivered drugs need not be produced in the highly sterile cleanroom environments required for injectables (Salama et al., 2006). Development of an oral delivery strategy for protein therapeutics would therefore be a boon to both patients and the protein therapeutics industry by offering improved patient quality of life and reduced cost.

Despite significant interest, the oral route has not yet been widely adopted with protein-based drugs because of the human body's natural mechanisms for breaking down ingested protein into substituent amino acids. The drug must first retain its structure and integrity through the highly acidic and proteolytic environment of the stomach, in which it spends an average time of around 3.5 hours (Dressman and Kramer, 2005). The drug then passes on to the small intestine, where it must remain stable in neutral conditions (pH 6.8-7.4), survive attack from additional proteolytic enzymes, pass through the mucosal lining, and cross the epithelial cell layer by either paracellular transport through the tight junctions or transcellular transport through the cells. The drug then enters the bloodstream, where it will be distributed throughout the body to perform its function. Because of this series of barriers, protein therapeutics exhibit extremely low bioavailability via the oral route without some means of protection (Morishita and Peppas, 2006; Renukuntla et al., 2013; Gupta et al., 2013).

Studies seeking to overcome these delivery barriers using pH-responsive hydrogels such as poly(methacrylic acid-grafted-poly(ethylene glycol)) (P(MAA-g-EG)) to deliver proteins have been relatively successful, but still suffer from low bioavailability compared to injection, resulting in wasted drug and therefore higher cost (Lowman et al., 1999; Carr et al., 2010; Carr and Peppas, 2010; Foss and Peppas, 2004; Kamei et al., 2009; Kavimandan et al., 2006). Furthermore, these hydrogels have not been optimized to deliver and release high molecular weight proteins. Clearly, there exists a need for improved methods of oral delivery of these high molecular weight therapeutic proteins.

SUMMARY OF THE INVENTION

The present invention overcomes limitations in the prior art by providing, in some aspects, improved compositions and methods for the generation and loading of polymer hydrogels that may be used, e.g., to deliver a therapeutic protein to a mammalian or human patient via an oral administration route. The invention is based, in part, on the observation of improved material responsiveness and delivery capacity for delivery of therapeutic proteins such as, e.g., factor VIII or factor IX. In some embodiments and as shown in the below examples, pH-sensitive polymers are provided in some embodiments that may be advantageously used to orally deliver factor IX.

In one aspect, the present disclosure provides a composition comprising:
(A) a therapeutic protein; wherein the therapeutic protein is greater than 30 kDa in size or the therapeutic protein is factor IX or factor VIII; and
(B1) a copolymer comprising methacrylic acid and poly(ethylene glycol) monomethyl ether monomethacrylate crosslinked with tetra(ethylene glycol) dimethacrylate (TEGDMA) or poly(ethylene glycol) dimethacrylate (PEGDMA) wherein the poly(ethylene glycol) component has an average molecular weight of about 100-1,000; or
(B2) a copolymer comprising methacrylic acid and poly(ethylene glycol) monomethyl ether monomethacrylate crosslinked with a poly(ethylene glycol) dimethacrylate (PEGDMA) wherein the poly(ethylene glycol) component has an average molecular weight of about 100-1,000.

In some embodiments, the therapeutic protein is factor IX; and the copolymer comprises methacrylic acid and poly(ethylene glycol) monomethyl ether monomethacrylate crosslinked with tetra(ethylene glycol) dimethacrylate (TEGDMA) or poly(ethylene glycol) dimethacrylate (PEGDMA). In other embodiments, the therapeutic protein is factor VIII; and the copolymer comprises methacrylic acid and polyethylene glycol) monomethyl ether monomethacrylate crosslinked with tetra(ethylene glycol) dimethacrylate (TEGDMA) or poly(ethylene glycol) dimethacrylate (PEGDMA). In some embodiments, the therapeutic protein is greater than 30 kDa in size; and the copolymer comprises methacrylic acid and poly(ethylene glycol) monomethyl ether monomethacrylate crosslinked with said poly(ethylene glycol) dimethacrylate (PEGDMA). In some embodiments, the composition is comprised in a pharmaceutical preparation formulated for oral administration. In some embodiments, the copolymer comprises poly(ethylene glycol) monomethyl ether monomethacrylate, wherein the poly(ethylene glycol) component has an average molecular weight of about 200 to about 2,000. In some embodiments, the average molecular weight is from about 400 to about 1,600. In some embodiments, the average molecular weight is from about 800 to about 1,200. In some embodiments, the average molecular weight is about 1,000. The ratio of the molar percentage of methacrylic acid (MAA) to poly(ethylene glycol) monomethyl ether monomethacrylate may be from about 1:1 to about 60:1. In some embodiments, the ratio of the molar percentage of methacrylic acid to poly(ethylene glycol) monomethyl ether monomethacrylate is from about 20:1 to about 40:1. In some embodiments, the copolymer comprises from about 0.1% to about 5% of crosslinking. In some embodiments, the copolymer comprises from about 0.5% to about 2.5% of crosslinking. In some embodiments, the copolymer comprises from about 0.5% to about 1.5% of crosslinking. In some embodiments, the copolymer is crosslinked with tetra(ethylene glycol) dimethacrylate. In some embodiments, the copolymer is crosslinked with poly(ethylene glycol) dimethacrylate, wherein the poly(ethylene glycol) component has an average molecular weight of about 100 to about 1,000. In some embodiments, the average molecular weight is from about 200 to about 600. In some embodiments, the average molecular weight is about 400. In some embodiments, the copolymer comprises from about 90 mol % to about 99 mol % methacrylic acid. In some embodiments, the copolymer comprises from about 95 mol % to about 98 mol % methacrylic acid. In some embodiments, the copolymer comprises from about 96.5 mol % to about 97.5 mol % methacrylic acid. In some embodiments, the copolymer comprises from about 1 mol % to about 10 mol % poly(ethylene glycol) monomethyl ether monomethacrylate. In some embodiments, the copolymer comprises from about 2 mol % to about 5 mol % poly(ethylene glycol) monomethyl ether monomethacrylate. In some embodiments, the copolymer comprises from about 2.5 mol % to about 3.5 mol % poly(ethylene glycol) monomethyl ether monomethacrylate. In some embodiments, the molecular weight of the therapeutic protein is greater than about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 kDa, or has a molecular weight having any range derivable therein. In some embodiments, the therapeutic protein is factor IX. In some embodiments, the therapeutic protein is factor VIII. In some embodiments, the composition comprises greater than about 20 μg of therapeutic protein per mg of copolymer. In some embodiments, the composition comprises greater than about 30 μg of therapeutic protein per mg of copolymer. In some embodiments, the copolymer has a particle size less than 100 μm. In some embodiments, the particle size less than 90 μm. In some embodiments, the particle size is less than 75 μm. In some embodiments, the particle size is less than 50 μm. In some embodiments, the copolymer begins swelling at a pH greater than about 5. In some embodiments, the pH is greater than about 6. In some embodiments, the composition releases greater than about 0.1 μg of therapeutic protein per mg of copolymer at pH 7.4. In some embodiments, the composition releases greater than about 0.25 μg of therapeutic protein per mg of copolymer at pH 7.4. In some embodiments, the therapeutic protein is factor VIII or IX and further comprises a targeting compound selected from an antibody, lectin, protein, or small molecule. In some embodiments, the targeting compound promotes bioadhesion. In some embodiments, the targeting compound is a lectin. In some embodiments, the lectin is wheat germ agglutinin. In some embodiments, the therapeutic protein is factor IX. In some embodiments, the therapeutic protein is factor VIII.

In another aspect, the present disclosure provides a method of treating hemophilia in a patient comprising orally administering a pharmacologically effective amount of a polymer comprising a therapeutic protein (e.g., factor IX or factor VIII) of the present invention to a patient in need of such treatment. In some embodiments, the patient is a human. In some embodiments, the hemophilia is hemophilia B. In other embodiments, the hemophilia is hemophilia A.

In still another aspect, the present disclosure provides a method of preparing the composition of the present invention, comprising:
  (i) polymerizing methacrylic acid and poly(ethylene glycol) monomethyl ether monomethacrylate in the presence of a crosslinking agent to produce the copolymer; and
  (ii) loading the copolymer with a therapeutic protein comprising incubating the copolymer with the therapeutic protein and wherein the therapeutic protein is factor VIII, factor IX, or a protein greater than 30 kDa.

In some embodiments, the polymerization of step (i) comprises:
  (a) admixing methacrylic acid with polyethylene glycol) monomethyl ether monomethacrylate to a solvent;
  (b) adding the crosslinking agent;
  (c) exposing the solution to UV radiation under conditions sufficient to cause polymerization to produce a copolymer.

In some embodiments, the copolymer is washed with deionized water. In some embodiments, the copolymer is dried in air. In some embodiments, the copolymer is dried under vacuum. In some embodiments, the copolymer is crushed using a mortar and pestle and sieved into microparticles. In some embodiments, the solvent is a 1:1 mixture of water and ethanol. In some embodiments, the method comprises admixing a ratio of methacrylic acid and poly(ethylene glycol) monomethyl ether monomethacrylate to solvent of 50:50 w/w. In some embodiments, the ratio of methacrylic acid and poly(ethylene glycol) monomethyl ether monomethacrylate is from about 20:1 to about 40:1. In some embodiments, the method comprises adding from about 0.5% to about 5% of the crosslinking agent. In some embodiments, the crosslinking agent is tetra(ethylene glycol) dimethacrylate or polyethylene glycol) dimethacrylate. In some embodiments, the method further comprises adding an initiator with the crosslinking agent. In some embodiments, the initiator is IRGACURE 184®. In some embodiments, the loading of the therapeutic protein comprises adding a solution of about 1:1 w/w to about 1:10 w/w of the copolymer to the therapeutic protein. In some embodiments, the solution comprises about 6.5:1 of the copolymer to the therapeutic protein. In some embodiments, the loading of the therapeutic protein further comprises rinsing the composition with an acid. In some embodiments, the acid is 0.1 N HCl. In some embodiments, the loading of the therapeutic protein further comprises drying the composition. In some embodiments, the composition is dried under vacuum at a temperature from about 25° C. to about 50° C. In other embodiments, the composition is dried by lyophilization. In some embodiments, the therapeutic protein is factor VIII. In some embodiments, the therapeutic protein is factor IX.

As used herein the specification, "a" or "an" may mean one or more. As used herein in the claim(s), when used in conjunction with the word "comprising", the words "a" or "an" may mean one or more than one.

As used in this application, the term "average molecular weight" refers to the relationship between the number of moles of each polymer species and the molar mass of that species. In particular, each polymer molecule may have different levels of polymerization and thus a different molar mass. The average molecular weight can be used to represent the molecular weight of a plurality of polymer molecules. Average molecular weight is typically synonymous with average molar mass. In particular, there are three major types of average molecular weight: number average molar mass, mass average molar mass, and Z-average molar mass. In the context of this application, unless otherwise specified, the average molecular weight represents either the number average molar mass or mass average molar mass of the formula. In some embodiments, the average molecular weight is the number average molar mass. In some embodiments, the average molecular weight is relative to one or more portions of the polymer (e.g. the molecular weight of a PEG component present in one or more monomers that may be polymerized to produce a polymer). In some embodiments, the average molecular weight may be used to describe a PEG component present in a crosslinker (e.g. the PEG component present in PEGDMA).

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term. "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
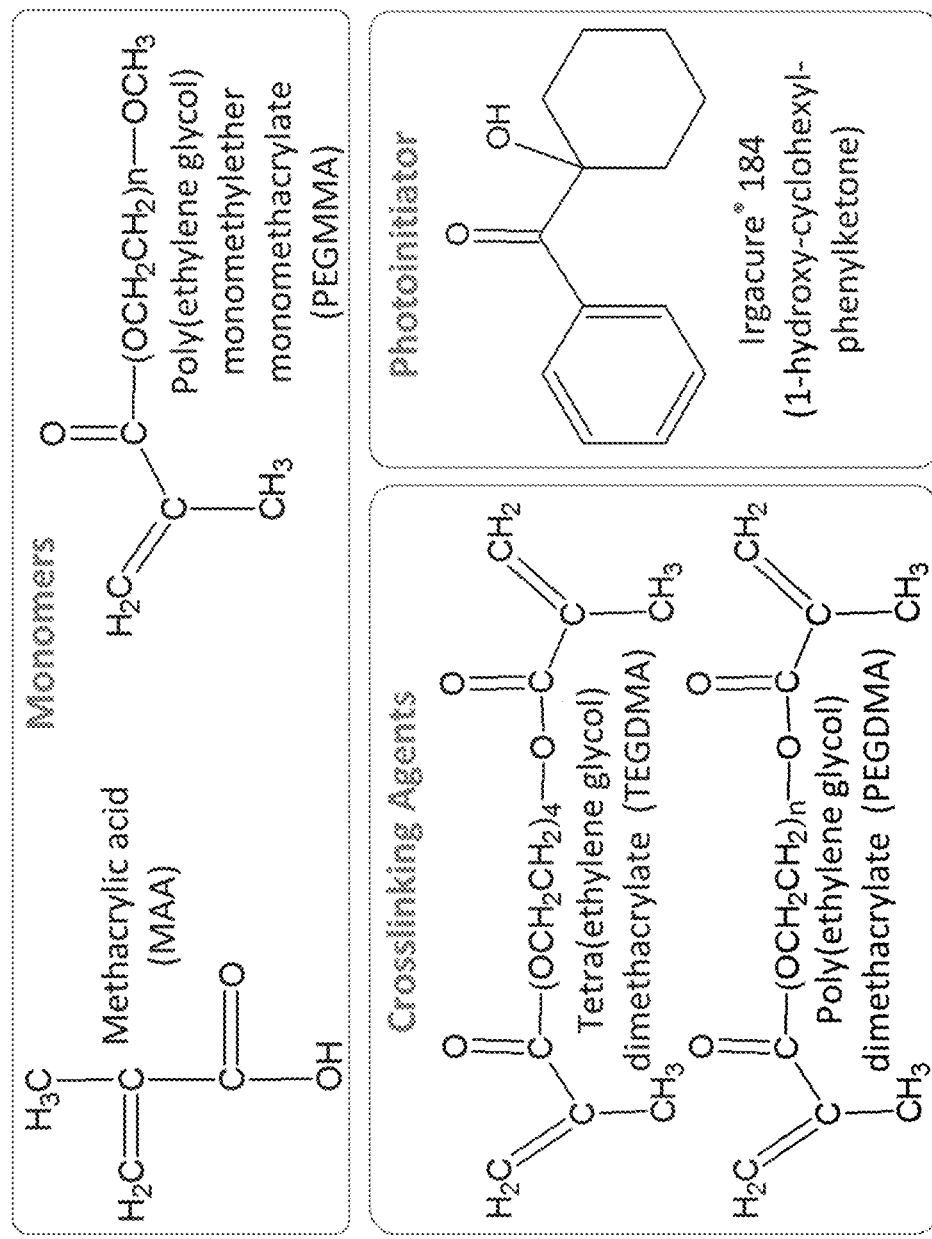
FIG. 1. Structures of polymer components

The present invention, in various aspects, overcomes limitations in the prior art by providing improved compositions and methods for oral delivery of therapeutic proteins, such as factor VIII or factor IX. For example, as shown in the below examples, improved hydrogels and methods of loading hydrogels with therapeutic proteins are provided and may be used, e.g., to enable improved oral delivery of high molecular weight proteins such as, for example, factor VIII or factor IX. In some embodiments, pH-sensitive copolymer hydrogels comprised of poly(methacrylic acid-grafted-poly (ethylene glycol)) (P(MAA-g-EG)) have been developed which are effective as drug delivery carriers for high molecular weight proteins.

I. HYDROGEL COPOLYMERS

In some aspects of the present invention, improved hydrogel polymers are provided. In some embodiments, the hydrogel polymer compositions may be used to for oral delivery of a drug, such as a protein therapeutic. The drug or protein therapeutic may require at least some protection from degradation in the digestive system; for example, the therapeutic protein may need protection from the acid conditions (e.g., pH ~2) found in the stomach. As shown in the below examples, hydrogel polymers are provided that may protect the drug or therapeutic protein while it is in transit through the acidic conditions in the stomach, and then the polymer can swell in the more basic conditions of the small intestine and allow for release of the drug or therapeutic protein in the small intestine. In some preferred embodiments, the protein is a factor VIII or factor IX. The polymers provided herein may be included in or used as a variety of pharmaceutical compositions, such as compositions for oral delivery, e.g., particles, tablets, capsules, caplets, gel-seals, lozenges, syrups, sprays, and other liquid dosage forms.

Generally, the hydrogels may comprise hydrophilic polymers or copolymers in the form of networks that can swell due to a high affinity for water; however, the hydrogel may be substantially insoluble due to the incorporation of chemical or physical crosslinks or other tie-points that keep the chains together and do not allow them to dissolve in water. Polymers or copolymer hydrogels may be responsive to pH changes. For example, in a solution with a lower pH (e.g., pH ~1-2), pH-sensitive hydrogel networks may be largely hydrated, similar to other hydrophilic copolymers; however, at higher pHs (e.g., at pH ~6-7), carboxylic acid groups present in the polymer or copolymer may deprotonate, and thus the polymer may attract more water into the polymer network. Thus, the increased absorption of water into the polymer or copolymer may result in swelling, thus increasing the distance between the copolymer chains. This increase in size, or swelling, can allow increased release of a drug or therapeutic protein from the hydrogel network. The hydrogels may thus be used to orally deliver a drug or therapeutic protein, such that at least a portion of the drug or therapeutic protein is substantially protected from acidic conditions in the stomach and then released in the small intestine.

As shown in the below examples, hydrogel polymers or copolymers comprising methacrylic acid (MAA) (e.g., a P(MAA-co-EG) or P(MAA-g-EG) polymer) can be optimized to deliver high molecular weight proteins such as factor VIII or IX. In some preferred embodiments, the copolymer is a P(MAA-co-EG) or P(MAA-g-EG) polymer. As shown in the below examples, these hydrogel polymers or copolymers may be used to load and release of therapeutic proteins which have a molecular weight of greater than 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 kDa, or any range derivable therein. In some embodiments, the molecular weight of the therapeutic proteins is greater than 50 kDa. In some embodiments, the therapeutic protein is factor IX. In other embodiments, the therapeutic protein is factor VIII. Additional details regarding monomers and hydrogels that may be used in various embodiments of the present invention may be found, e.g., in WO 2008/055254, which is incorporated by reference herein in its entirety without disclaimer.

In some embodiments, the copolymer comprises a polymer of only the monomers referred to in the copolymer name; for example, the P(MAA-co-PEGMMA) copolymer may be composed of a polymer made from only methacrylic acid (MAA) and poly(ethylene glycol) methyl ether monomethacrylate (PEGMMA) In some embodiments, as a polyacrylate polymer, the methacrylate component of the PEGMMA monomer is polymerized into the backbone of the copolymer with methacrylic acid (MAA) as the other monomer component. Nonetheless, as would be recognized by one of skill in the art, other monomers such as, e.g., an acrylic acid monomers may be included in the copolymer, without substantially altering one or more of the properties (e.g., loading and release of a drug or therapeutic protein, etc.) of the copolymer. In some embodiments, since the methacrylic unit is on one end of the PEG chain, it is contemplated that the PEG chain of the PEGMMA is graft or tether. As used herein, the term "copolymer" refers to a polymer that comprises at least about 75%, more preferably at least about 80%, more preferably at least about 85%, more preferably at least about 90%, or at least about 91, 92, 93, 94, 95, 96, 97, 98, 99, or 99.5% of the monomers stated in the name of the copolymer (e.g., methacrylic acid and poly (ethylene glycol) methyl ether monomethacrylate in P(MAA-co-PEGMMA). Additional monomers that may be included in a copolymer include:
(i) acrylic acid or acrylate monomers such as, e.g., acrylic acid, methacrylic acid (2-methylprop-2-enoic acid, MAA), ethacrylic acid, propacrylic acid, crotonic acid ((E)-but-2-enoic acid), methacrylate (2-methylprop-2-enoate), methyl methacrylate, (Z)-3-cyclohexylbut-2-enoic acid, butylmethacrylate (butyl 2-methylprop-2-enoate),
(ii) poly(ethylene glycol) (P(EG) or PEG), polyethylene glycol) methyl ether monomethacrylate or polyethylene glycol) monomethyl ether monomethacrylate (PEGMMA or EG), and/or polyethylene glycol) methacrylate (PEGMA), or
(iii) itaconic acid.

The hydrogel polymers or copolymers are, in some preferred embodiments, at least partially crosslinked. In some embodiments, the polymers or copolymers may be from about 0.5-10%, 0.5-7.5%, 0.5-4%, 0.5-2%, 1-2%, 1.25-2%, 1-1.75%, 1.25-1.75%, or about 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, or 5% (Molar % crosslinker), or any range derivable therein of a crosslinker used to crosslink the copolymer. In some embodiments, less than about 2% or from about 0.25 to less than 2% of a crosslinker used to crosslink the copolymer; for example, as shown in the below embodiments, improved characteristics (e.g., protein release from polymer) was observed for larger therapeutic proteins such as factor IX when using less than about 2% crosslinker. A variety of crosslinkers are known and may be included in hydrogel polymers or copolymers of the present invention. For example, diacrylates, such as, e.g., tetra(ethylene glycol) dimethacrylate (TEGDMA), poly(ethylene glycol) dimethacrylate (PEGDMA), ethylene glycol dimethacrylate (EGDMA), 1,3-butanediol dimethacrylate, 1,4-butanediol diacrylate, 1,4-butanediol dimethacrylate, 1-(acryloyloxy)-3-(methacryloyloxy)-2-propanol, or 1,3-glyceryl dimethacrylate are crosslinkers that may be used to crosslink select hydrogel polymers or copolymers of the present invention. While in some embodiments, the crosslinker is an EGDMA (e.g., PEGDMA, EGDMA, or TEGDMA), it is anticipated that virtually any suitably hydrophilic diacrylate may be used in some embodiments. In some embodiments, the crosslinker is poly(ethylene glycol) dimethacrylate (PEGDMA) and is polymerized into the backbone of the copolymer chain due to the methacrylate unit on each end of the PEG chain. In some embodiments, TEGDMA is used as the crosslinker.

In some aspects, the hydrogel polymer comprises a monomer or a crosslinker containing a poly(ethylene glycol) unit. In some embodiments, one of the monomers is a PEG containing molecule such as poly(ethylene glycol) monomethyl ether methacrylate (PEGMMA) which has a formula:

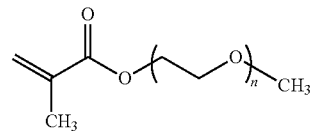

wherein: the portion of the molecule described by (—CH$_2$CH$_2$O—)$_n$ above has an average molecular weight from about 40 to about 4,000. The structure of this compound is also shown in FIG. 1. In some embodiments, the average molecular weight is from about 100-1,000, 200-2,000, 200-600, 400-1,200, 200, 250, 300, 350, 400, 450, 500, 550, 600, 800, 850, 900, 950, 1,000, 1,050, 1,100, 1,150, or 1,200, or any range derivable therein. In some embodiments, n is 15, 16, 17, 18, 19, 20, 21, 22, 23, 24, 25, 26, 27, 28, 29, or 30. As such these molecules contain an amount of repeats necessary to obtain a polymer composition with a particular average molecular weight. As would be obvious to a person of skill in the art, the polymer composition may comprise a plurality of different starting monomers which each have different repeat length but the average of the molecular weight of each of those monomers is equal to the average molecular weight of the solution. It is contemplated that several different length monomers can be incorporated into a single polymer as would be readily obvious to a person of skill in the art. These average molecular weights often refer to the entire monomer or to only the polymeric portion of the monomer (e.g. the PEG component). Additionally, it is contemplated that either the methylated or free hydroxyl form of the PEG group in the monomer, as described above, may be used. Without being bound by theory, it is contemplated that both version would produce similar results in delivery large molecular weight therapeutic proteins. Similarly, the crosslinking agent, poly(ethylene glycol) dimethacrylate, which has a formula:

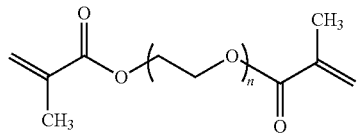

wherein: the portion of the molecule described by (—CH$_2$CH$_2$O—)$_n$ above has an average molecular weight from about 40 to about 2,000, can exist as a variety of different polymer lengths within a given composition so long as the entire composition has an average molecular weight within the given range. In some embodiments, n is 4, 5, 7, 8, 9, 10, 11, 12, 13, or 14. The structure for this compound is also shown in FIG. 1. In some embodiments, the average molecular weight is from about 100-2,000, 100-1,000, 200-600, 200, 250, 300, 350, 400, 450, 500, 550, 600, 800, 900, or 1,000, or any range derivable therein. In some instances, the crosslinker possesses a precise number of repeating units in the PEG portion of the molecule; for example, tetra(ethylene glycol) dimethacrylate has four repeating ethylene glycol units. Without wishing to be bound by any theory, the size of the crosslinking agent may be used to affect the mesh size of the crosslinked polymer network and/or modify or optimize the loading and release ability of the polymer.

The ratio of monomers present in a copolymer may vary. For example, when two monomers comprise the majority of a copolymer (e.g., the methacrylic acid and poly(ethylene glycol) monomethyl ether methacrylate monomers present in a P(MAA-co-EG) or P(MAA-g-EG) copolymer, etc.), the ratio of the monomers may vary, e.g., from about 1:1-50:1, 20:1-40:1, or 20:1, 25:1, 26:1, 27:1, 28:1, 29:1, 30:1, 31:1, 32:1, 33:1, 34:1, 35:1, or about 40:1, or any range derivable therein (e.g., for the ratio of MAA:EG present in a P(MAA-co-EG) or P(MAA-g-EG) copolymer). As shown in the below examples, particularly beneficial properties were observed for P(MAA-co-EG) or P(MAA-g-EG) copolymers that comprised a ratio of from about 25:1 to about 35:1 of MAA:EG present in the copolymer displayed significantly improved properties (e.g., loading and release of a therapeutic protein); in some embodiments, the P(MAA-co-EG) or P(MAA-g-EG) copolymer may have a ratio of about 1:1-50:1, 20:1-40:1, or 20:1, 25:1, 30:1, 35:1, or about 40:1 MAA:EG, or any range derivable therein. As shown in the below examples, P(MAA-co-EG) or P(MAA-g-EG) copolymers having a ratio of about 30:1. In some embodiments, the copolymer is P(MAA-co-EG) or P(MAA-g-EG) having a ratio of from about 20:1 to about 40:1 of MAA:EG and comprising about 0.5-3% (Molar %) of the TEGDMA or PEGDMA crosslinker.

Furthermore, in some embodiments, the copolymer can be modified with one or more targeting compounds which direct or bias the copolymer towards adhesion or distribution towards a particular cell type, tissue, or organ. Some non-limiting examples of targeting compounds which can be attached to the copolymer including antibodies, antibody fragments, small molecules (e.g. estrogen, glucose, folic acid, a vitamin, a cofactor, or a small molecule therapeutic agent), lectins, peptides, or proteins. In some embodiments, the targeting compound is a lectin (e.g. wheat germ agglutinin). It is contemplated that these targeting compounds may be attached to the copolymer using a linker and a protein based interaction such as the interaction between biotin and avicin. The attached of targeting compounds to a hydrogel is described by Wood, et al., 2006; Wood, et al., 2008; and Wood, et al., 2010, all of which are incorporated herein by reference.

Polymerization reactions to polymerize monomers may be performed using methods known to one of skill in the art such as, e.g., using UV light to promote polymerization, in some embodiments, the following reaction may be used to polymerize monomers. Polymerizations may be carried out in an about 50:50 w/w mixture of water and ethanol. Within this cosolvent, monomers may be added at various molar ratios, along with crosslinker (e.g., 0.1-5 mol %) and 1 mol % initiator. For example, a photo-initiator such as Irgacure 184® may be used. Molar percent is defined with regard to the total moles of each of the monomers between each other and between the monomers and crosslinker. The monomer solution may then be introduced into a nitrogen environment and purged with nitrogen to remove oxygen, a free radical scavenger. The solution may then be pipetted between two quartz glass plates (e.g., 15×15×0.3 cm) separated by a Teflon spacer (e.g., 0.7 mm thick), and then polymerized, e.g., for a period of time from about 10 minutes to about 120 minutes in 35 mW/cm$^2$ UV light using a UV flood source. In some embodiments, the time period is about 30 minutes. The hydrogel may then be removed from the glass plates. The hydrogel may be then punched into 10 mm diameter disks. The hydrogel may be washed with deionized water (e.g., in 1 L of 18.2 MΩ-cm), changed daily for several days (e.g., 7-10 days) to remove unreacted monomers. Furthermore, the hydrogel may be dried in air for about 3 days Following washing, the films may be dried under vacuum at 37° C. for at least 3 days, crushed into microparticles (e.g., with a mortar and pestle), and sieved to a desired size (e.g., about 45-75 μm in size). Depending on the particular formulation, it may be desired to sieve the microparticles of dried hydrogel copolymer into a range of desired sizes, e.g., about 45-300, 50-200, 75-175, 45-90, 45-150, 75-150, 90-150 μm, <90 μm, 75-90 μm, <75 μm, 45-75 μm, <45 μm, 35-45 μm, or about 20, 25, 30, 35, 40, 45, 50, 55, 60, 65, 70, 75, 80, 85, 90, 100, 110, 120, 130, 140, 150 μm, or any range derivable therein. Without wishing to be bound by any theory, the particular size (e.g. less than about 90 μm) of the microparticles may provide one or more advantages to the administration, loading, or release properties of the hydrogel copolymer and the therapeutic protein.

In some embodiments, the hydrogel copolymers may be used as or included in a pharmaceutical composition. It is envisioned that the pharmaceutical composition may include one or more additional agent such as a starch, cellulose, or flavoring, etc. As such, these compositions may be formulated with an inert diluent or with an assimilable edible carrier, or they may be enclosed in hard- or soft-shell gelatin capsule, or they may be compressed into tablets, or they may be incorporated directly with the food of the diet. In certain embodiments, the hydrogel copolymer may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings can reduce denaturation of the composition in the stomach or upper bowel where the pH is acidic. See, e.g., U.S. Pat. No. 5,629,001. Upon reaching the small intestines, the basic pH therein can substantially or completely dissolve the coating and permits the composition to be released. A syrup may contain a hydrogel copolymer and a sweetening agent (e.g., sucrose), a preservative (e.g., methyl or propylparabens), a dye, and/or flavoring cherry or orange flavor, etc.). Typically, any material used in preparing a dosage unit form should be substantially pharmaceutically pure and substantially non-toxic in the amounts employed.

II. THERAPEUTIC PROTEINS

In some embodiments, the hydrogel copolymers may comprise or contain a therapeutic protein. The therapeutic protein may be a natural and nonnatural (e.g., recombinant) proteins, polypeptides, and peptides. The proteins may, by themselves, be incapable of passing (or which pass only a fraction of the administered dose) through the gastrointestinal mucosa or may be susceptible to chemical cleavage by acids or enzymes in the gastrointestinal tract or both. In addition to proteins, the hydrogel network also may include polysaccharides, and particularly mixtures of mucopolysaccharides, carbohydrates, lipids; other organic compounds. For therapeutic applications, the protein may be biologically active. In some embodiments, the protein may be a protein that has a molecular weight of greater than 30 kDa.

Examples of proteins that may be comprised in a hydrogel copolymer of the present invention include, but are not limited to, synthetic, natural, or recombinant sources of: a growth hormone-releasing hormone an interleukin (e.g., IL-1 beta); a growth factor (e.g., STEMGEN® (ancestim; stem cell factor); a basic fibroblast growth factor (e.g. high molecular weight FGF-2), a hepatocyte growth factor; erythropoietin (e.g., PROCRIT®, EPREX®, or EPOGEN® (epoetin-α); ARANESP® (darbepoetin-α); NEORECORMON®, EPOGIN® (epoetin-β); and the like); a blood factor (e.g., ACTIVASE® (alteplase) tissue plasminogen activator; NOVOSEVEN® (recombinant human factor VIIa); Factor Nina; Factor VIIa (e.g., KOGENATE®); Factor IX (e.g., BENEFIX®, RIXUBIS™, ALPROLIX™); hemoglobin; and the like); an antigen; an antibody (e.g., a monoclonal antibody) (e.g., RITUXAN® (rituximab); REMICADE® (infliximab); HERCEPTIN® (trastuzumab); HUMIRA™ (adalimumab); XOLAIR® (omalizumab); BEXXAR® (tositumomab); RAPTIVA™ (efalizumab); ERBITUX™ (cetuximab); and the like), an scFv region, or an antibody fragment, including an antigen-binding fragment of a monoclonal antibody; a soluble receptor (e.g., a TNF-α-binding soluble receptor such as ENBREL® (etanercept); a soluble VEGF receptor; a soluble interleukin receptor; a soluble γ/δ T cell receptor; and the like); an enzyme (e.g., α-glucosidase; CERAZYME® (imiglucarase; β-glucocerebrosidase, CEREDASE® (alglucerase); an enzyme activator (e.g., tissue plasminogen activator); an angiogenic agent (e.g., vascular endothelial growth factor (VEGF); an anti-angiogenic agent (e.g., a soluble VEGF receptor); thrombopoietin; glial fibrillary acidic protein; a follicle stimulating hormone; a human alpha-1 antitrypsin; a leukemia inhibitory factor; a transforming growth factor; a tissue factor; a macrophage activating factor, a neutrophil chemotactic factor; fibrin; a leukemia inhibitory factor; or a protease inhibitor (e.g., $\alpha_2$-macroglobulin). Combinations, analogs, fragments, mimetics or polyethylene glycol (PEG)-modified derivatives of these compounds, or other derivatives of any of the above-mentioned substances may also be suitable. Also, fusion proteins comprising all or a portion of any of the foregoing proteins are suitable for use in the hydrogel copolymer described herein. One of ordinary skill in the art, with the benefit of the present disclosure, may recognize additional drugs, including drugs other than proteins, which may be useful in the compositions and methods of the present disclosure. Such drugs are still considered to be within the spirit of the present disclosure.

In some embodiments, the therapeutic protein is factor IX. As a protein, factor IX is, by itself, generally unsuitable for oral administration because it would be substantially broken down, cleaved, denatured, and/or inactivated in the digestive tract. Factor IX is a protein involved clotting processes and defective forms of the protein can lead to the inability for blood to properly clot. Thus, clotting disorders (such as hemophilia) are typically treated by intravenous administration of factor IX, a mutant form of factor IX, or a recombinant form of factor IX to a patient. Factor IX is implicated in the biological pathway leading to clotting disorders. Hemophilia B results from a mutant form of the gene which encodes for factor IX leading to a deficiency in factor IX. Treatment of hemophilia B may include administration of a form of factor IX to the patient to replace the deficient form. In some embodiments of the present invention, injections of factor IX may be advantageously avoided by orally administering factor IX, a mutant form of factor IX, or a recombinant form of factor IX in a polymer of the present invention to a patient in need of a factor IX therapy.

Additionally, in some embodiments, the therapeutic protein is factor VIII. Similarly, to factor IX, as a protein, factor VIII is generally unsuitable for oral administration. factor VIII is also involved in the biological pathways which facilitate blood coagulation, and defective forms of factor VIII can lead to disease states. In particular, a detective form of factor VIII or a deficiency of factor VIII is implicated in hemophilia A. Treatment of hemophilia A may include the administration of factor VIII to the patient to replace the patient's defective or deficient form. In some embodiments, injections of factor VIII may be advantageously avoided by orally administering factor VIII, a mutant form of factor VIII, or a recombinant form of factor VIII in a polymer of the present invention to a patient in need of a factor VIII therapy.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Materials and Methods 1.1 Synthesis of Hydrogels

In order to synthesize P(MAA-g-EG) hydrogels, a monomer solution containing methacrylic acid (MAA) and poly (ethylene glycol) (MW=1000) monomethyl ether monomethacrylate (PEGMMA) in a 1:1 ratio of hydrogen bonding groups was first prepared in an amber bottle. (The structures of all components are shown in FIG. 1.) A crosslinking agent—tetraethylene glycol dimethacrylate (TEGDMA), polyethylene glycol) (MW=400) dimethacrylate (PEGDMA400), polyethylene glycol) (MW=600) dimethacrylate (PEGDMA600), or poly(ethylene glycol) (MW=1000) dimethacrylate (PEGDMA1000)—was added at 0.80 to 2.0 mol % of total monomers. TEGDMA has four ethylene glycol repeat units, PEGDMA400 has nine, PEGDMA600 has 14, and PEGDMA1000 has 23, and therefore incorporating a crosslinking agent with a longer PEG chain allows for a larger mesh size. Crosslinking density is inversely related to mesh size (i.e. higher crosslinking density, smaller mesh/pore size). The solvent was a 50:50 w/w mixture of water and ethanol and was added in a 50:50 w/w ratio of total monomer to solvent. Lastly, the photo-initiator, Irgacure 184® (1-hydroxycyclohexyl phenyl ketone), was added at 1.0 wt % of total monomers. After all components are added, the prepolymer solution was sonicated for 20 minutes to fully dissolve the solid PEGDMMA and IRGACURE 184®. The solution was then placed in an MBraun glove box in an oxygen-deficient environment and purged with nitrogen for 5 minutes to remove oxygen, which is a free radical scavenger. Remaining in the sealed glove box, the solution was pipetted between two glass slides, which were separated with a 0.7 mm Teflon® spacer and held together with clips. The prepolymer solution in the glass plates was exposed to UV light for 30 minutes to allow for polymerization. After synthesis, the resulting polymer was removed from the glass plate, and 10 mm diameter disks were punched. Both the film and disks were washed in deionized water for 7 to 10 days to remove any unreacted monomer. After rinsing, the polymer was dried in air for 3 days, followed by drying at 37° C. under vacuum for 3 days. The dried films were crushed using a mortar and pestle and sieved into microparticles of the following size ranges: 35-45 µm, 45-75 µm, <75 µm, 75-90 µm, and 90-150 µm. The disks were used for further characterization studies.

1.2. Characterization of Hydrogels

Microparticles were characterized by scanning electron microscopy (SEM), potentiometric titration, and Fourier transform infrared spectroscopy (FTIR). SEM was used to examine the surface morphology and size distribution of the microparticles. For SEM sample preparation, vacuum-dried microparticles were dusted onto carbon tape-covered aluminum stubs. Samples were coated with 10 nm of Pt/Pd using a Cressington 208 Benchtop sputter coater. SEM images were obtained using a Zeiss Supra 40 VP Scanning Electron Microscope.

The polymeric composition was analyzed using potentiometric titration and FTIR. Potentiometric titration was used to quantify the MAA content of the hydrogels. A 3.33 mg/mL solution of microparticles in deionized water, same concentration as that used for loading studies, was titrated to pH 11 using 0.2 N NaOH at 25° C. with constant stirring. The 0.2 N NaOH was standardized with potassium hydrogen phthalate. NaOH was added (10-60 µL) to the microparticle solution, and the pH was measured at each step. The pH value was recorded when a steady value (±0.01) was reached in three consecutive readings. The molar amount of MAA was calculated based on the equivalence point and a charge balance.

FTIR is a surface analysis technique that was used to confirm polymer composition. Vacuum dried microparticles were added at 1-2.5 wt % to crushed and dried potassium bromide (KBr), and samples were pressed into disks. FTIR spectra were obtained using a Thermo Mattson Infinity Gold spectrometer. Background spectra of KBr only were subtracted from all sample spectra. FTIR was performed fir all formulations.

1.3. pH Responsive Behavior of Hydrogels

Dynamic swelling studies were performed using a series of 0.1 M 3,3-dimethylglutaric acid (DMGA) buffers between pH 1.2 and 7.6 at constant ionic strength heated to 37° C. The polymer disks were stepped through the series of buffers in order of increasing pH, mimicking the pH gradient along the GI tract. The disk remained in each buffer for 10 minutes and were blotted and weighed between each step. The weight swelling ratio, q, is the swollen weight divided by the dried weight. In order to determine the swelling profile, the weight swelling ratio was calculated at each pH value.

1.4. Cytocompatibility Studies

The cytocompatibility of the microparticles was assessed in a Caco-2 cell culture and a HT29-mTX cell culture, separately, using an CellTiter 96® AQueous One Solution Cell Proliferation Assay (MTS). Caco-2 cells at passages between 50-65 was plated on a 96 well plate at an initial seeding density of $10^5$ cells/well. Cells were grown for 2 days in modified. Dulbecco's Eagle Medium (DMEM) without phenol red. Separately, microparticles were sterilized under UV for 10 minutes prior to (preparing microparticle solutions. Microparticles were added to DMEM without phenol red at concentrations of 1.25, 2.5, and 5 mg/mL and allowed to swell overnight. After 2 days of culturing, growth media was removed, and 100 µL/well of microparticle solutions (n=4 for each formulation and concentration), media (positive control, n=8), or water (negative control, n=4) was applied to the cells. After a 2-hour or 6-hour incubation period, 20 µL/well of MTS was added, and then incubated for an additional 90 minutes. The absorbance was read at 490 nm for MTS and 690 nm for background using a plate reader. Cell viability was calculated as relative absorbance which is a ratio of the absorbance of the treatment group to that of the positive control. No appreciable cytotoxicity is defined as a relative absorbance of 0.8.

1.5. Therapeutic Loading Studies

P(MAA-g-EG) particles at a concentration of 3.33 mg particles/mL solution were added to a 0.5 mg/mL factor IX protein solution, and the mixtures were placed on a rotator in an incubator at 37° C. for 6 or 2.4 hours. The particles were then collapsed with 0.1 N hydrochloric acid (HCl), triple rinsed with 0.1 N HCl, and collected by centrifugation. The particles were dried either by being lyophilized overnight or placed under vacuum at 37° C. overnight. The protein-loaded particles were stored at −80° C. Samples for protein analysis were collected prior to starting loading, as well as after the allotted time for loading, after collapsing, and after each rinse. Modifications to the loading protocol included a 5 mg particle/mL solution, incubation at 4° C. for 5 days, and collection by Buchner filter.

1.6. Therapeutic Release Studies

The protein-loaded particles were placed in 0.1 N HCl (pH 2) on a rotator at 37° C. for 1 hour. The particles were then collected by centrifugation and the solution was collected as a sample for protein analysis. Then, 1×PBS buffer was added to the particles, and the pH was adjusted to pH 7.4. For the duration of the release study, the particle mixtures remained rotating at 37° C. Samples were collected at various time points ranging for 5 minutes to 24 hours. After each sample was removed, an equal volume amount of 1×PBS was added back to maintain constant volume.

Additional release studies were conducted following a two-stage dissolution procedure using biorelevant media. Biorelevant media were prepared using a FaSSIF, FeSSIF & FaSSGF Powder (Biorevelant.com) which contains bile salts and phospholipids. Simulated gastric fluid (SGF) was prepared at a 1× concentration with a final pH of 1.6 according to the manufacturer's protocol (Biorelevant). Fasted-state simulated intestinal fluid (FaSSIF) was prepared at 2× concentration with a final pH of 6.9. The dissolution test was performed using an USP apparatus 2 (paddles) setup for small volume (100 mL vessel) with low evaporation mini vessel covers using a Distek 2100B dissolution apparatus. A 5 mg sample of hFIX-loaded microparticles was added to a sigmacoted vessel containing 30 mL of SGF (1×, pH 1.8) warmed to 37° C. After 30 minutes, 30 mL of FaSSIF (2×) warmed to 37° C. was added, raising the pH to 6.5. The solution was continuously stirred at 75 rpm and maintained at 37° C. for both the SGF and FaSSIF stages. The FaSSIF stage was carried out for up to 6 h. After each sample was removed, an equal volume of media was added back to maintain a constant volume.

1.7. Protein Quantification and Analysis

Human factor IX (hFIX) was quantified using a hFIX-specific ELISA (AssayPro LLC) according to the manufacturer's protocol. The hFIX-specific ELISA can detect hFIX in plasma, serum, cell culture supernatant, and protein concentrates, allowing this assay to be applicable to loading and release studies, as well as in vitro and in vivo studies. For all quantification methods, samples were tested in triplicate.

Figure 2:
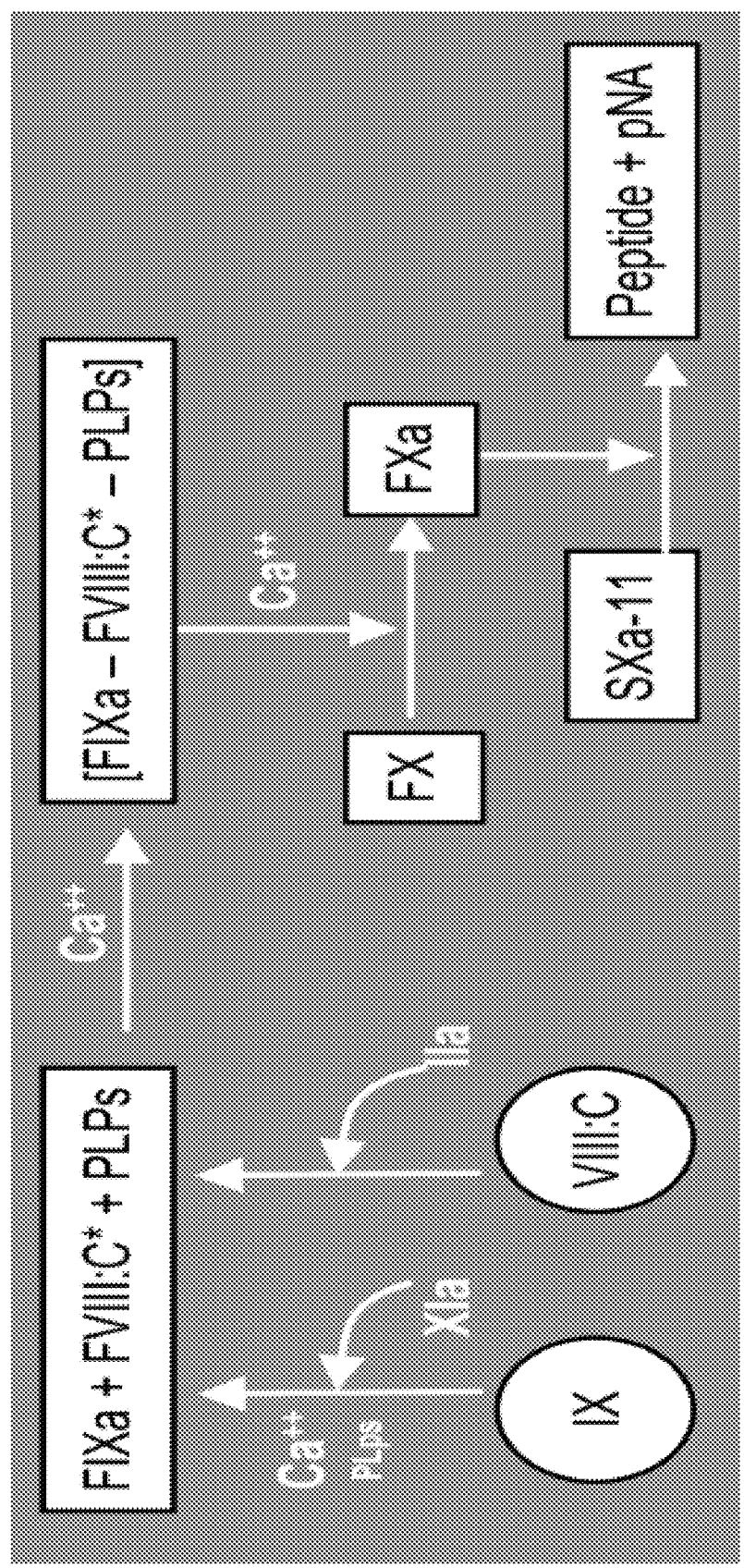
FIG. 2. Reaction scheme for the factor IX chromogenic assay as described in the Aniara manual (Aniara, 2014)

In addition to protein quantification, it is also critical to ensure that the protein remains active after release in order to serve its purpose as a protein replacement therapy. hFIX activity was determined using a factor IX chromogenic assay according to the manufacturer's protocol (Aniara). Any biological fluid and protein concentrates are also suitable samples for this assay. The principle of this chromogenic assay relies on a portion of the coagulation cascade (shown in FIG. 2), where the enzymatic activity is directly related to FIX, the limiting factor. The generated factor Xa (FXa) can be quantified with high sensitivity (detection range 0.1-30 ng/mL) based on its specific activity on factor Xa chromogenic substrate (SXa-11). FXa can cleave the substrate to release a pNA chromophore. The free pNA can be quantified by color development at 405 nm. The amount of FIX in the sample is linearly related to the FXa activity, as measured by the amount of pNA released. An endpoint method by acid quenching the reaction or an initial-rate method by use of a kinetic recording spectrophotomer can be used to measure the concentration of free pNA. This chromogenic assay was run using a 96-well plate format with all samples done in triplicate.

Additional protein structural features were evaluated to further determine the state of the protein during loading and after release. Native protein gel electrophoresis were performed to confirm the protein primary structure, as well as to detect any protein aggregation. Protein samples were prepared with Novex® Tris-Glycine Native Sample Buffer and loaded into a Novex® Tris-Glycine gel (8% acrylamide). Protein gels were run in Novex® Tris-Glycine Native Running Buffer at constant voltage (125 V) for 1 to 3 hours using the XCell SureLock™ mini-cell electrophoresis system, according to the manufacturer's protocol (Life Technologies). The protein gel was stained with SYPRO® Ruby protein gel stain and will be imaged by exciting at 280 nm. Samples from both loading and release were run.

Example 2

Figure 3:
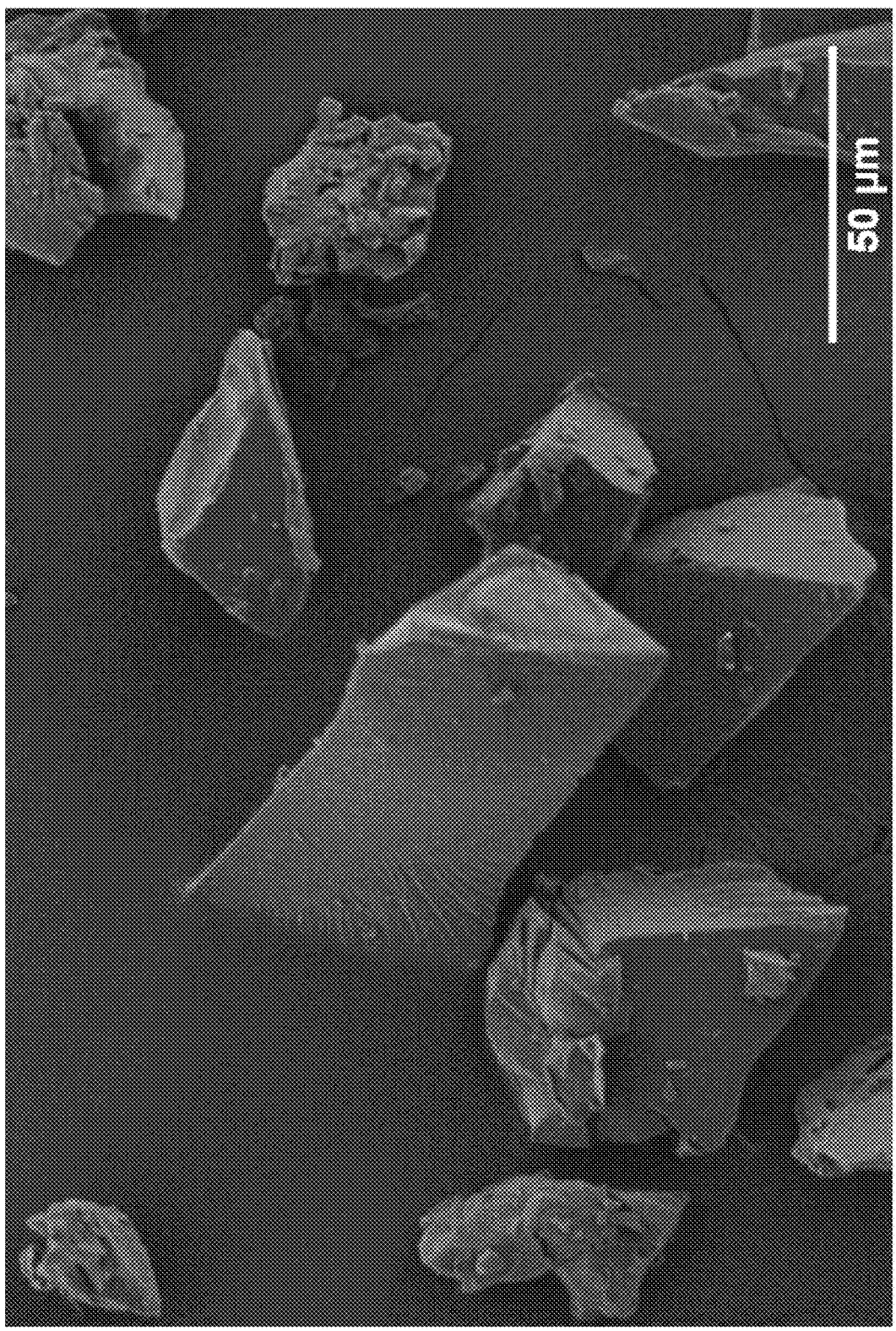
FIG. 3. SEM micrograph shows a wide polydispersity of size and morphology of 45-75 μm microparticles.

Results of Hydrogel Synthesis and Use in the Delivery of Factor IX 1.1. Hydrogel Synthesis and Characterization P(MAA-g-EG) hydrogels were synthesized with MAA and PEGMMA monomers and crosslinked with either TEGDMA or PEGDMA400 ranging from 0.8-2.0 mol %. SEM micrograph (FIG. 3) of crushed P(MAA-g-EG) particles (45-75 μm) shows irregular morphology due to the crushing process. Additionally, the wide polydispersity of microparticle size can be attributed to sieving which only defines two of the three dimensions.

Figure 4:
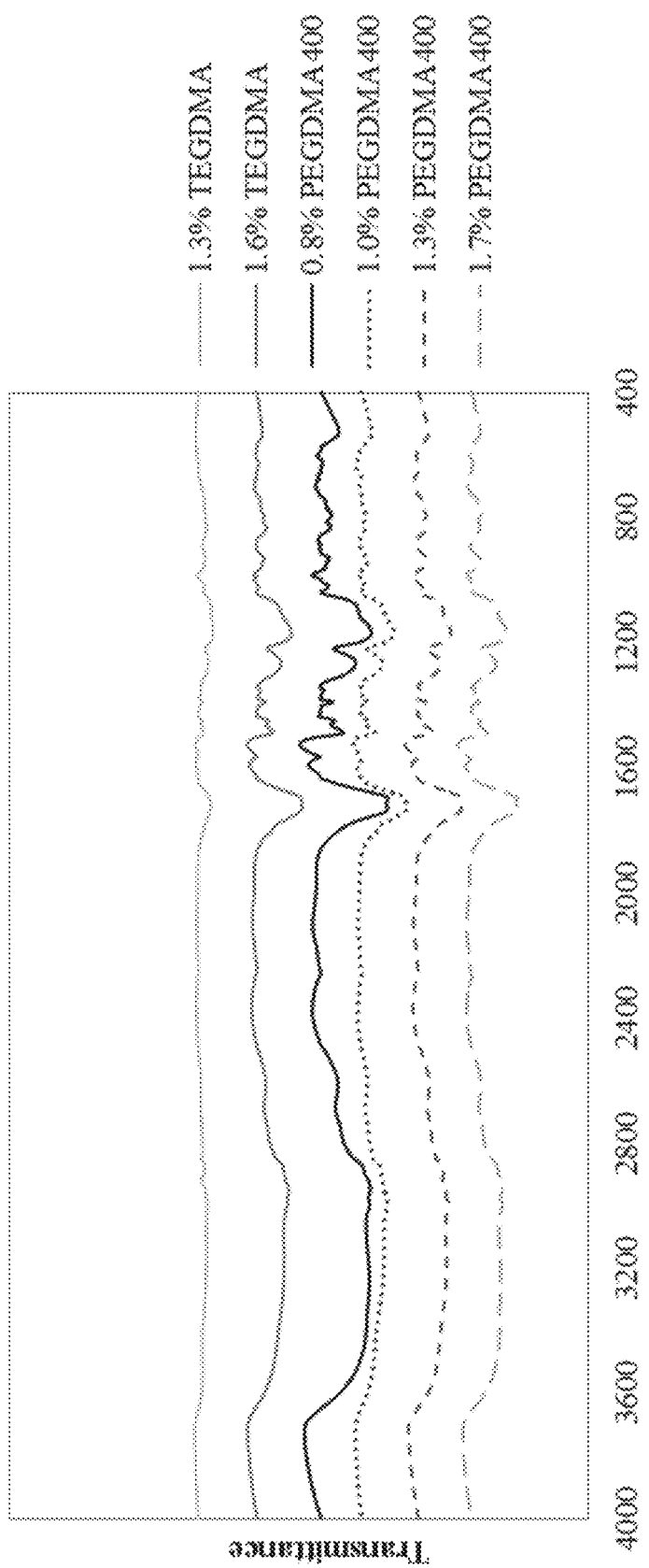
FIG. 4. Fink spectra of the instant hydrogels such as crosslinked P(MAA-g-EG) copolymers.
Figure 5:
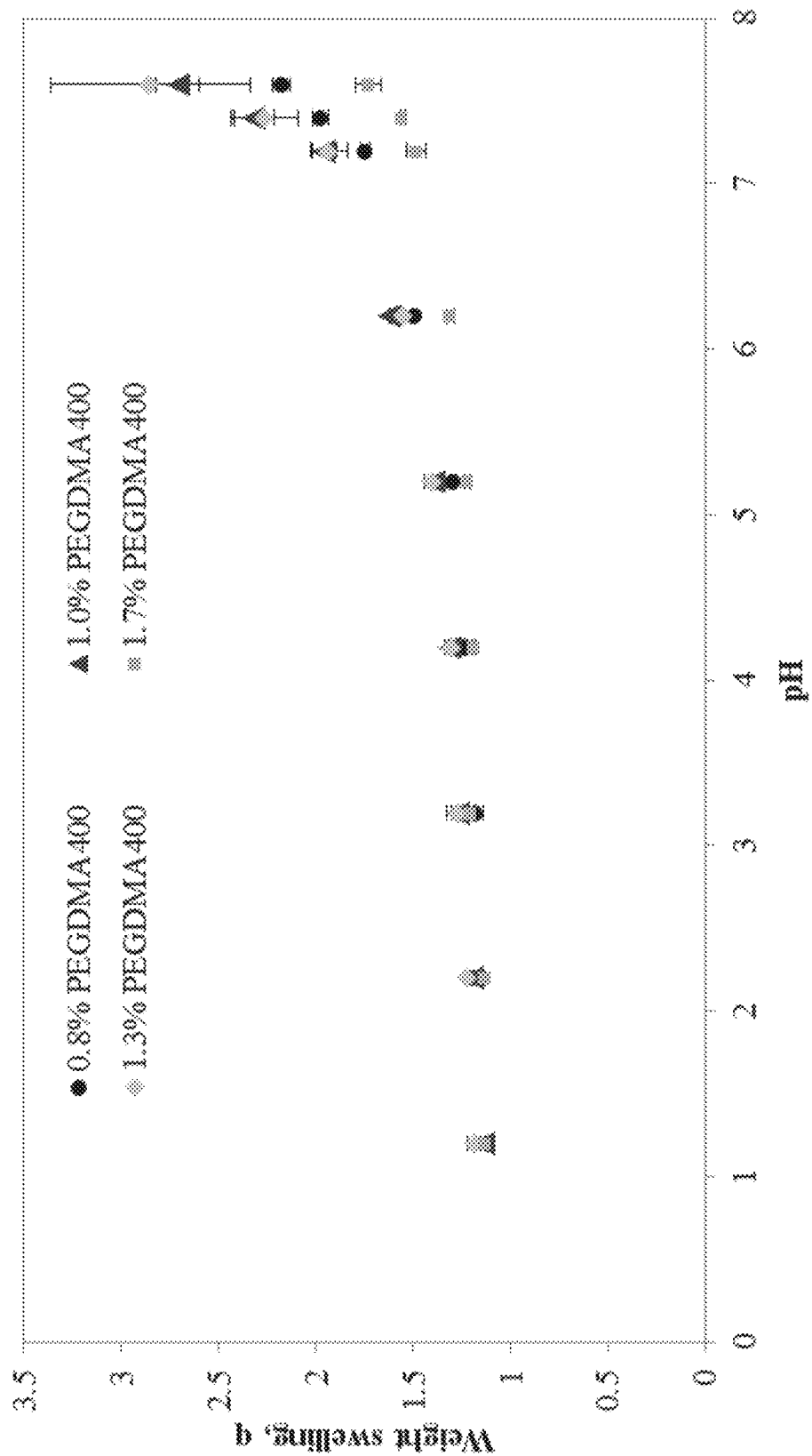
FIG. 5. Dynamic swelling curves indicate pH-responsiveness of the instant P(MAA-g-EG) hydrogels.

FTIR spectra of crosslinked P(MAA-g-EG) shows characteristics associated with MAA and PEG. As shown in FIG. 4, the wide band in the 2800-3600 cm$^{-1}$ is attributed to stretching of hydrogen bonded carboxylic acid dimers (2800-3100 cm$^{-1}$) of MAA and stretching of hydroxyl groups (3200-3600 cm$^{-1}$) of PEG. The band at 1700 cm$^{-1}$ is attributed to stretching of carboxylic acid. The bands at 1300-1450 cm$^{-1}$ are due to scissoring and bending of alkanes of PEG. FIG. 5 shows the dynamic swelling behavior of P(MAA-g-EG) hydrogels. All formulations remained collapsed at low and swelling began to increase above pH 5-6 (as shown in FIG. 5), which is desirable for oral delivery applications. Based on the potentiometric titration results, all hydrogel formulations had 96.5-97.0 mol % MAA and MAA:PEG molar ratios of 27.3-32.8 (Table 1). Since PEGMMA has 45 ether groups and MAA has one carboxyl group, the desired ratio for equivalent hydrogen bonding groups is approximated to 44 mol MAA to 1 mol PEGMMA.

TABLE 1

Quantification of MAA by potentiometric titration.

| Sample | mol % MAA | mol % PEG | MAA:PEG |
| --- | --- | --- | --- |
| 1.3% TEGDMA | 96.51 | 3.49 | 27.7 |
| 1.6% TEGDMA | 96.47 | 3.08 | 31.5 |
| 0.8% PEGDMA400 | 96.97 | 3.23 | 30.0 |
| 1.0% PEGDMA400 | 96.52 | 3.53 | 27.3 |
| 1.3% PEGDMA400 | 96.56 | 3.48 | 27.7 |
| 1.7% PEGDMA400 | 97.04 | 2.96 | 32.8 |
| 2.0% PEGDMA400 | 96.92 | 3.44 | 28.1 |

1.2. Cytocompatibility

Figure 6:
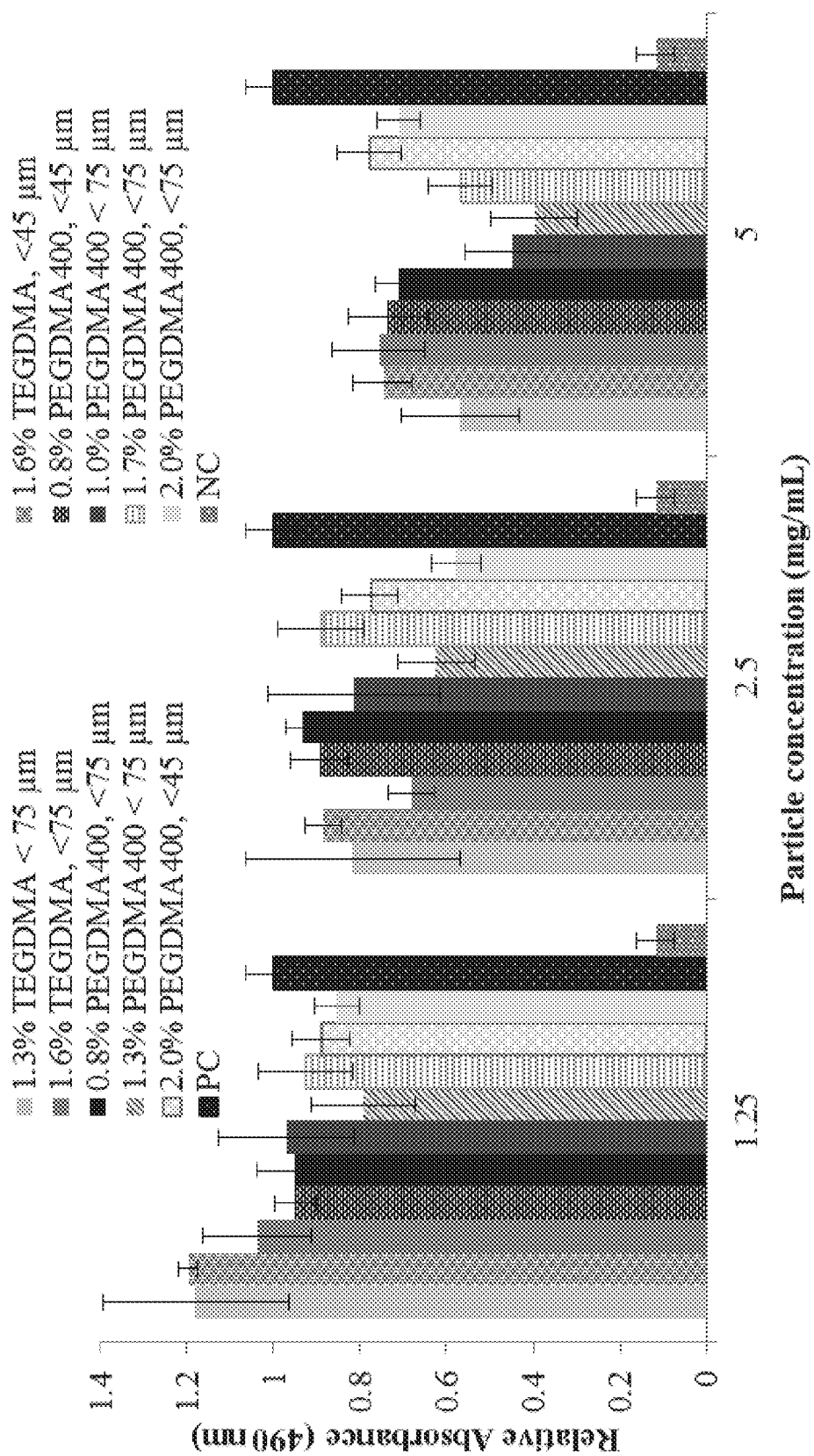
FIG. 6. Cytocompatibility of P(MAA-g-EG) microparticles with Caco-2 cells after a 2-hour incubation is concentration dependent.
Figure 7:
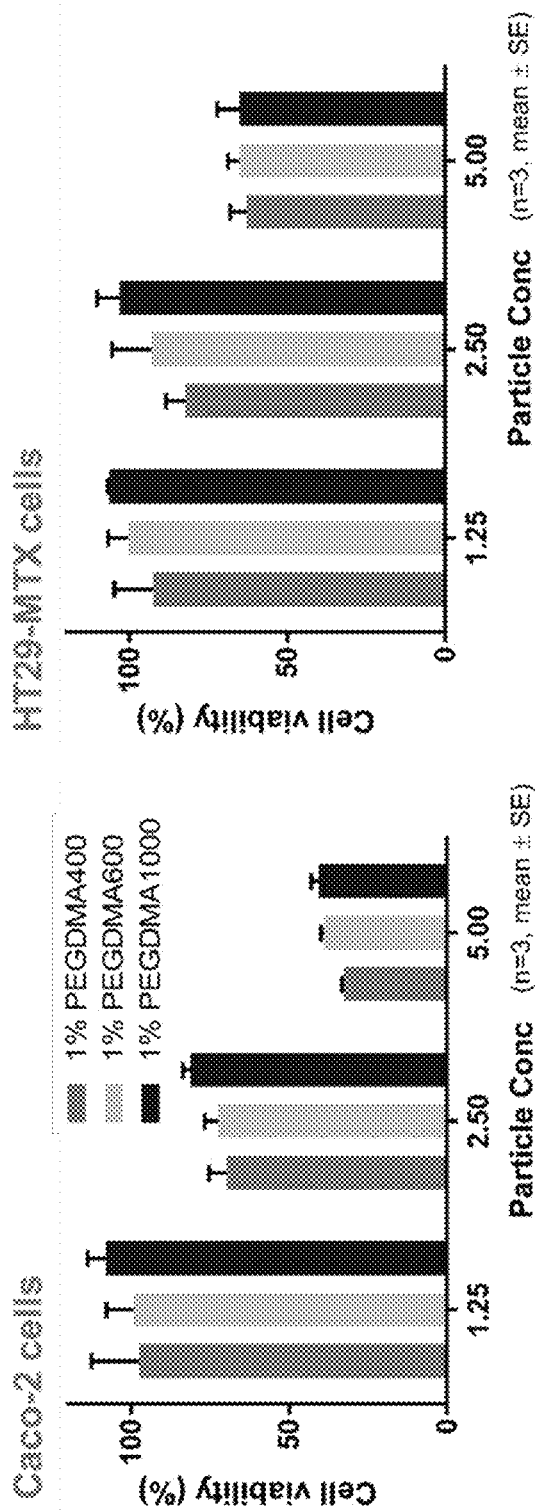
FIG. 7: P(MAA-g-EG) microparticles are cytocompatible with both Caco-2 cells and HT29-MTX cells after a 6-hour incubation.

Cytocompatibility was evaluated in Caco-2 cells or HT29-MTX cells, separately, using an MTS assay. Exposure (2 hours) to lower concentrations (1.25 and 2.5 mg/mL) of all particle formulations did not show appreciable cytotoxicity (e.g. at least 80% viability or 0.8 relative absorbance). Studies were also preformed for both <45 μm and <75 μm microparticles confirmed that cytotoxicity is concentration dependent and that low concentrations are cytocompatible (FIG. 6). Additionally, 35-45 µm microparticles were cytocompatible at low concentrations after a 6-hour incubation (FIG. 7).

1.3. Drug Loading/Release

Figure 8:
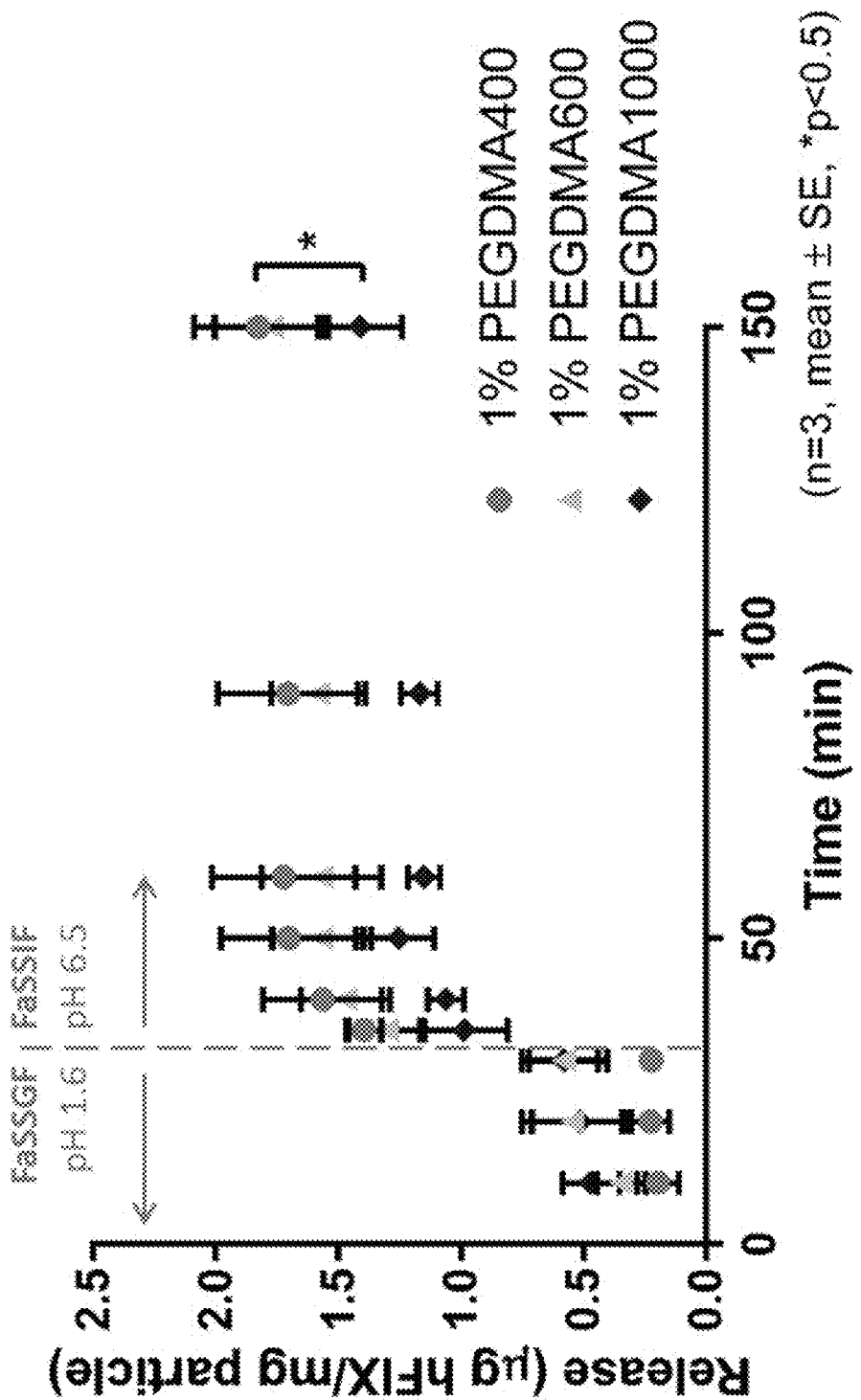
FIG. 8: Release of factor IX from P(MAA-g-EG) microparticles using two-stage dissolution in biorelevant media shows the desired release profile.
Figure 9:
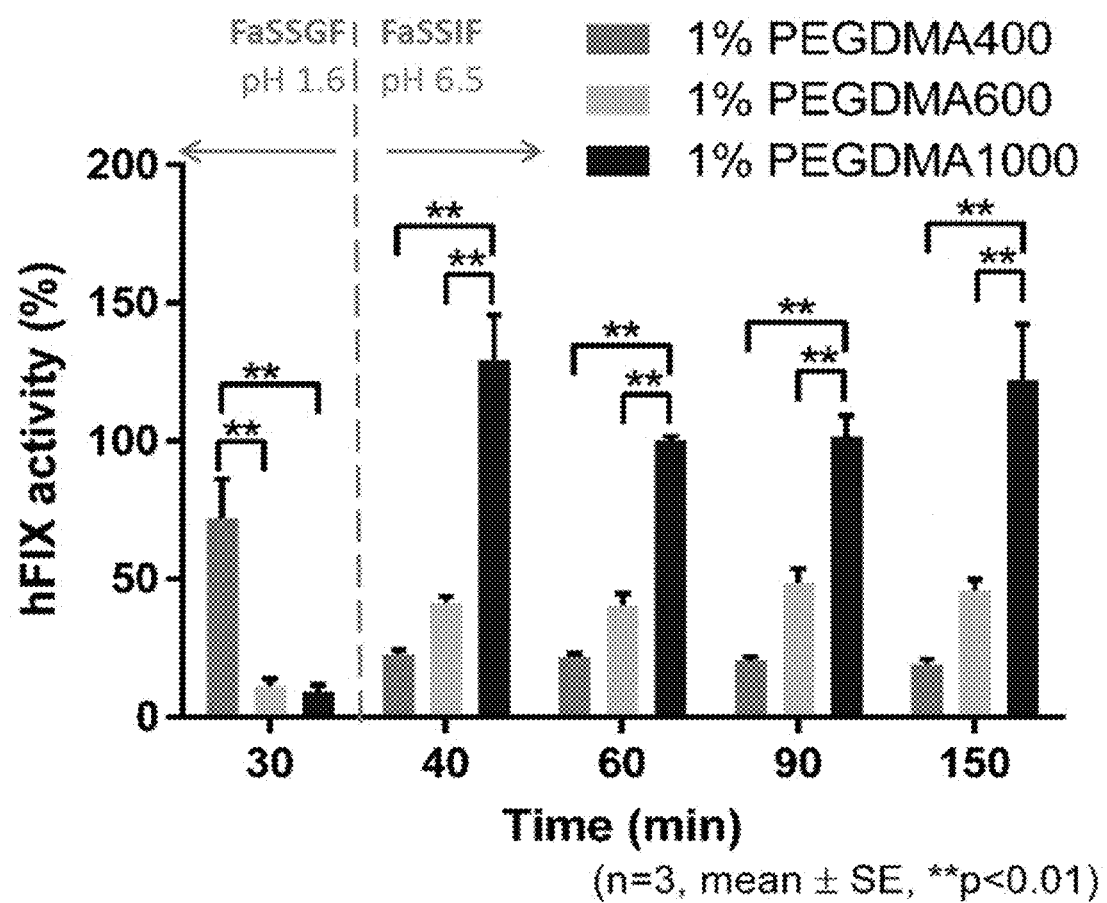
FIG. 9: Activity of released factor IX can be maintained in the intestinal conditions.

Loading and release studies for factor IX have been performed using microparticles (<45 µm) with different crosslinking densities and crosslinking agents (Table 2). As indicated by the results, release was significant in the pH 7.4 solution as compared to the pH 2 solution. Any release at pH 2 is likely due to protein bound to the surface of the particles. The major of the release occurred in the pH 7.4 solution when the hydrogels were in the swollen state. Both the loading level and release (µg FIX/mg particle) generally follow a trend based on crosslinking density, where less crosslinking (i.e. larger mesh size) corresponded to higher loading level and delivery capability. The P(MAA-g-EG) formulation with 0.8 mol % PEGDMA400 resulted in 60.02 µg FIX loaded per mg particle and in 10.55 µg FIX released per mg particle. A chromogenic assay was also performed for all samples (after loading, after collapsing, after rinsing, after 1 h release in pH 2, and after 6 h release in pH 7.4) for each formulation to determine the FIX activity. Based on the absorbance measurements, the all samples from after 6 h of loading and from after 6 h release in pH 7.4 indicated detectable activity, with the exception of release from the 2.0% PEGDMA400 formulation. Samples after collapsing, rinsing, and release in pH 2 indicated no detectable activity. Release of factor IX tested using dissolution in biorelevant media showed minimal release in fasted simulated gastric conditions (FaSSGF) and increased release in fasted-state simulated intestinal conditions (FaSSIF) (FIG. 8). The activity of release factor IX is better maintained in the intestinal conditions as desired. Additionally, the maintenance of released factor IX activity was improved with an increased mesh size from a longer PEG chain in the crosslinking agent. (FIG. 8).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,629,001
U.S. Pat. No. 5,641,515
U.S. Pat. No. 5,792,451
U.S. Pat. No. 5,580,579
WO 2008/055254
Aniara Manual and Protocol for BIOPHEN Factor IXa, Aniara (West Chester, Ohio), 2014.
Artursson, and Karlsson, J., Correlation between oral drug absorption in humans and apparent drug permeability coefficients in human intestinal epithelial (Caco-2) cells. Biochem. Biophys. Res. Comm. 175, 880-885, 1991.
Artursson, P. Cell cultures as models for drug absorption across the intestinal mucosa. Crit. Rev. Therap. Drug Carrier Systems 8, 305-330, 1991.
Betancourt et al., Characterization of pH-responsive hydrogels of poly(itaconic acid-g-ethylene glycol) prepared by UV-initiated free radical polymerization as biomaterials for oral delivery of bioactive agents. J. Biomed. Mater. Res. 93A, 175-188, 2010.
Brannon-Peppas and Peppas, Equilibrium swelling behavior of pH-sensitive hydrogels. Chem. Eng. Set. 46, 715-722, 1991.
Carr and Peppas. Assessment of poly(methacrylic acid-co-N-vinyl pyrrolidone) as a carrier for the oral delivery of therapeutic proteins using Caco-2 and HT29-MTX cell lines. J. Biomed. Mater. Res. 92A, 504-512, 2010.
Carr and Peppas, Molecular Structure of Physiologically-Responsive Hydrogels Controls Diffusive Behavior. Macromol. Biosci. 9, 497-505, 2009.

TABLE 2

Results for loading and release of factor IX using <45 µm microparticles.

| | Loading (6 h) | | Release (pH 2, 1 h) | | Release (pH 7.4, 6 h) | |
| --- | --- | --- | --- | --- | --- | --- |
| Sample | Loading level (µg FIX/mg particle) | Loading efficiency (%) | Release (µg FIX/mg particle) | Release efficiency (%) | Release (µg FIX/mg particle) | Release efficiency (%) |
| 1.6% TEGDMA | 32.89 | 13.36 | 0.04 | 0.12 | 0.91 | 2.78 |
| 1.6% TEGDMA | 51.24 | 20.81 | 0.04 | 0.08 | 0.42 | 0.83 |
| 0.8% PEGDMA400 | 60.02 | 24.38 | 0.19 | 0.32 | 10.55 | 17.57 |
| 1.0% PEGDMA400 | 44.39 | 18.03 | 0.02 | 0.05 | 2.11 | 4.76 |
| 2.0% PEGDMA400 | 30.29 | 12.30 | 0.00 | 0.00 | 0.00 | 0.00 |

Carr et al., Complexation Hydrogels for the Oral Delivery of Growth Hormone and Salmon Calcitonin. Ind. Eng. Chem. Res. 49, 11991-11995, 2010.
Dantzig and Bergin, Uptake of the cephalosporin, cephalexin, by a dipeptide transport carrier in the human intestinal cell line, Caco-2. Biochim. Biophys. Acta 1027, 211-217, 1990.
Dimitrov, D. S., Therapeutic Proteins. Methods Mol. Biol. 899, 1-26, 2012.
Dressman and Kramer, Pharmaceutical Dissolution Testing. Taylor & Francis, Boca Raton, Fla., 2005.
Foss and Peppas, Investigation of the cytotoxicity and insulin transport of acrylic-based copolymer protein delivery systems in contact with caco-2 cultures. *Eur. J. Pharm. Biopharm.* 57, 447-455, 2004.

Foss. A. C., Goto, T., Morishita, M., Peppas, N. A., 2004. Development of acrylic-based copolymers for oral insulin delivery. *Eur. J. Pharm. Biopharm.* 57, 163-169, 2005.

FY Innovative Drug Approvals. 1-28, 2011.

Gupta et al., Oral delivery of therapeutic proteins and peptides: a review on recent developments. *Drug Deliv.* 20, 237-246, 2013.

Hidalgo et al., Characterization of the human colon carcinoma cell line (Caco-2) as a model system for intestinal epithelial permeability. *Gastroenterology* 96, 736-749, 1989.

Hwang et al., *Crit. Rev. Ther. Drug Carrier Syst.*, 15(3): 243-284, 1998.

Ichikawa and Peppas, Novel complexation hydrogels for oral peptide delivery: in vitro evaluation of their cytocompatibility and insulin-transport enhancing effects using Caco-2 cell monolayers. *J. Biomed Mater. Res.* 67A, 609-617, 2003.

Kamei et al., Complexation hydrogels for intestinal delivery of interferon β and calcitonin. *J. Control. Release* 134, 98-102, 2009.

Kavimandan and Peppas, Confocal Microscopic Analysis of Transport Mechanisms of Insulin Across the Cell Monolayer. *Int. J. Pharm.* 354, 143-148, 2008.

Kavimandan et al., Novel delivery system based on complexation hydrogels as delivery vehicles for insulin-transferrin conjugates. *Biomater.* 27, 3846-3854, 2006.

Leader et al., Protein therapeutics: a summary and pharmacological classification. *Nat. Rev.* 7, 21-39, 2008.

Lennernas et al., Comparison between active and passive drug transport in human intestinal epithelial (Caco-2) cells in vitro and human jejunum in vivo. *Int. J. Pharm.* 127, 103-107, 1996.

López and Peppas, Effect of Poly (Ethylene Glycol) Molecular Weight and Microparticle Size on Oral Insulin Delivery from P(MAA-g-EG) Microparticles. *Drug Dev. Ind. Pharm.* 30, 497-504, 2004.

Lowman et al., Oral Delivery of Insulin Using pH-Responsive Complexation Gels. *J. Pharm. Sci.* 88, 933-937, 1999.

Madsen and Peppas, Complexation graft copolymer networks: swelling properties, calcium binding and proteolytic enzyme inhibition. *Biomater.* 20, 1701-1708, 1999.

Mathiowitz et al., *Nature*, 386(6623):410-414, 1997.

Morishita and Peppas, Is the oral route possible for peptide and protein drug delivery?. *Drug Discov. Today* 11, 905-910, 2006.

Mullard, A., 2013. 2012. FDA drug approvals. *Nat. Rev. Drug Discov.* 12, 87-90.

Nakamura et al., Oral insulin delivery using P(MAA-g-EG) hydrogels: effects of network morphology on insulin delivery characteristics. *J. Control. Release* 95, 589-599, 2004.

Peyrot et al., Correlates of insulin injection omission. *Diabetes Care* 33, 240-245, 2010.

Pinto, M., Enterocyte-like differentiation and polarization of the human colon carcinoma cell line Caco-2 in culture. *Biol. Cell* 47, 323-330, 1983.

Renukuntla et al., Approaches fir enhancing oral bioavailability of peptides and proteins. *Int. J. Pharm.* 447, 75-93, 2013.

Salama et al., Tight junction modulation and its relationship to drug delivery. *Adv. Drug Deliv. Rev.* 58, 15-28, 2006.

Sambuy et al., The Caco-2 cell line as a model of the intestinal barrier: influence of cell and culture-related factors on Caco-2 cell functional characteristics. *Cell Biol. Toxicol.* 21, 1-26, 2005.

Torres- and Peppas, Molecular Design and in Vitro Studies of Novel pH-Sensitive Hydrogels for the Oral Delivery of Calcitonin. *Macromol.* 32, 6646-6651, 1999.

U.S. Food and Drug Administration, 2012

Wood et al., *Acta Biomaterialia*, 6:48-56, 2010.

Wood et al., *Biomacromolecules*, 9:1293-1298, 2008.

Wood et al., *J. Controlled Release*, 2:e66-e68, 2006.

Yee, S., In Vitro Permeability Across Caco-2 Cells (Colonic) Can Predict In Vivo (Small Intestinal) Absorption in Man—Fact or Myth. *Pharm. Res.* 14, 763-766, 1997.

Youn et al., Improved intestinal delivery of salmon calcitonin by Lys18-amine specific PEGylation: Stability, permeability, pharmacokinetic behavior and in vivo hypocalcemic efficacy. *J. Control. Release* 114, 334-342, 2006.

What is claimed is:

1. A composition comprising:
   (A) a therapeutic protein; wherein the therapeutic protein is factor IX or factor VIII; and
   (B1) a copolymer comprising methacrylic acid and poly(ethylene glycol) monomethyl ether monomethacrylate crosslinked with about 0.8-1.0% poly(ethylene glycol) dimethacrylate (PEGDMA) wherein the poly(ethylene glycol) component of the PEGDMA has an average molecular weight of about 300-500.

2. The composition of claim 1, wherein the therapeutic protein is factor IX.

3. The composition of claim 1, wherein the therapeutic protein is factor VIII.

4. The composition of claim 1, wherein the composition is comprised in a pharmaceutical preparation formulated for oral administration.

5. The composition of claim 1, wherein the ratio of the molar percentage of methacrylic acid (MAA) to poly(ethylene glycol) monomethyl ether monomethacrylate is from about 1:1 to about 60:1.

6. The composition of claim 5, wherein the ratio of the molar percentage of methacrylic acid to poly(ethylene glycol) monomethyl ether monomethacrylate is from about 20:1 to about 40:1.

7. The composition of claim 1, wherein the copolymer comprises from about 90 mol % to about 99 mol % methacrylic acid.

8. The composition of claim 7, wherein the copolymer comprises from about 96.5 mol % to about 97.5 mol % methacrylic acid.

9. The composition of claim 1, wherein the copolymer comprises from about 1 mol % to about 10 mol % poly (ethylene glycol) monomethyl ether monomethacrylate.

10. The composition of claim 9, wherein the copolymer comprises from about 2.5 mol % to about 3.5 mol % poly(ethylene glycol) monomethyl ether monomethacrylate.

11. The composition of claim 1, wherein the composition comprises greater than about 20 µg of therapeutic protein per mg of copolymer.

12. The composition of claim 11, wherein the composition comprises greater than about 30 µg of therapeutic protein per mg of copolymer.

13. The composition of claim 1, wherein the copolymer has a particle size less than 100 µm.

14. The composition of claim 13, wherein the particle size is less than 50 µm.

15. The composition of claim 1, wherein the copolymer swelling increases at a pH greater than about 5.

16. The composition of claim 1, wherein the composition releases greater than about 0.1 μg of therapeutic protein per mg of copolymer at pH 7.4.

17. The composition of claim 16, wherein the composition releases greater than about 0.25 μg of therapeutic protein per mg of copolymer at pH 7.4.

18. The composition of claim 1, wherein the therapeutic protein is factor VIII or IX and further comprises a targeting compound selected from an antibody, lectin, protein, or small molecule.

19. The composition of claim 18, wherein the targeting compound promotes bioadhesion.

20. The composition of claim 18, wherein the targeting compound is a lectin.

21. The composition of claim 20, wherein the lectin is wheat germ agglutinin.

22. A method of treating hemophilia in a patient comprising orally administering a pharmacologically effective amount of the composition of claim 1 to a patient in need of such treatment.

\* \* \* \* \*